(12) United States Patent
Kim et al.

(10) Patent No.: US 9,012,228 B2
(45) Date of Patent: Apr. 21, 2015

(54) DISK-TYPE MICROFLUID SYSTEM AND METHOD FOR CHECKING BLOOD STATUS

(71) Applicant: Postech Academy-Industry Foundation, Pohang-si (KR)

(72) Inventors: Dong Sung Kim, Pohang-si (KR); Moonwoo La, Chuncheon-si (KR); Sangmin Park, Busan (KR)

(73) Assignee: Postech Academy-Industry Foundation, Pohang-Si (KR)

( * ) Notice: Subject to any disclaimer, the term of this patent is extended or adjusted under 35 U.S.C. 154(b) by 0 days.

(21) Appl. No.: 14/357,359

(22) PCT Filed: Dec. 12, 2012

(86) PCT No.: PCT/KR2012/010797
§ 371 (c)(1),
(2) Date: May 9, 2014

(87) PCT Pub. No.: WO2013/089433
PCT Pub. Date: Jun. 20, 2013

(65) Prior Publication Data
US 2014/0315317 A1   Oct. 23, 2014

(30) Foreign Application Priority Data

Dec. 12, 2011   (KR) .................. 10-2011-0133258

(51) Int. Cl.
*G01N 15/05*   (2006.01)
*G01N 35/00*   (2006.01)
(Continued)

(52) U.S. Cl.
CPC .............. *G01N 15/05* (2013.01); *G01N 33/491* (2013.01); *G01N 21/07* (2013.01); *G01N 11/02* (2013.01); *G01N 2011/008* (2013.01); *G01N 35/00069* (2013.01); *G01N 2015/055* (2013.01)

(58) Field of Classification Search
CPC ....... G01N 11/02; G01N 15/04; G01N 15/05; G01N 2011/008; G01N 2015/055; G01N 21/07; G01N 33/48; G01N 33/49; G01N 33/491; G01N 35/00069
USPC .............. 436/63, 70, 45, 164, 174, 177, 180; 422/64, 72, 73, 82.05, 502, 506, 527, 422/533, 548; 702/19
See application file for complete search history.

(56) References Cited

U.S. PATENT DOCUMENTS 6,506,606 B1 * 1/2003 Winkelman et al. ............ 436/70
6,709,869 B2 * 3/2004 Mian et al. ..................... 436/45
(Continued)

FOREIGN PATENT DOCUMENTS

KR    10-0350022    12/2002
KR    10-2009-0020086    2/2009
(Continued)

*Primary Examiner* — Maureen Wallenhorst
(74) *Attorney, Agent, or Firm* — Lexyoume IP Meister, PLLC

(57) ABSTRACT

Provided is a method for checking a blood status including: a step of supplying blood to the centrifugal container of a disk; a step of rotating the disk to centrifuge the blood cells and blood plasma in the centrifuge container, and detecting the actual moving distance per hour of the blood cells in the centrifugal container; and a step of establishing a first graph which represents the actual moving distance of the blood cells per hour, and a second graph which represents the theoretical moving distance of the blood cells per hour, and thereafter calculating the hematocrit of the blood cells and the viscosity of the blood plasma by comparing the first graph with the second graph.

3 Claims, 5 Drawing Sheets

(51) Int. Cl.
*G01N 33/49* (2006.01)
*G01N 11/02* (2006.01)
*G01N 21/07* (2006.01)
*G01N 11/00* (2006.01)

(56) References Cited

U.S. PATENT DOCUMENTS 7,422,693 B2 * 9/2008 Carter et al. .................. 210/745
7,790,110 B2 * 9/2010 Cho et al. ...................... 422/72
7,811,519 B2 * 10/2010 Shiga ............................ 422/72
2014/0020457 A1 * 1/2014 Dayel et al. ................. 73/61.68

FOREIGN PATENT DOCUMENTS

| KR | 10-0915195 | 8/2009 |
| KR | 10-2012-0061551 | 6/2012 |
| WO | 97/24066 | 7/1997 |

* cited by examiner

DISK-TYPE MICROFLUID SYSTEM AND METHOD FOR CHECKING BLOOD STATUS

TECHNICAL FIELD

The present invention relates to a disk-shaped microfluidic system and a method for checking a blood condition, and more particularly, to a disk-shaped microfluidic system and a method for checking a blood condition that extracts plasma by centrifuging blood.

BACKGROUND ART

Generally, blood separation, plasma extraction, property analysis of blood, and the like are performed by equipment or apparatuses suitable for respective purposes. The blood is divided into the plasma and blood cells by an apparatus such as a centrifuge, and the divided plasma is extracted by pipetting and the like. Further, properties of the blood such as viscosity, hematocrit, and the like of the blood may be analyzed by dedicated equipment for measuring each property.

A series of processes through the dedicated equipment have an advantage of more accurately performing each process, but there are disadvantages that in order to check the blood condition, a large amount of blood may be used, and a long testing time for checking all blood conditions is taken due to non-continuous processes.

The above information disclosed in this Background section is only for enhancement of understanding of the background of the invention and therefore it may contain information that does not form the prior art that is already known in this country to a person of ordinary skill in the art.

DISCLOSURE

Technical Problem

The present invention has been made in an effort to provide a disk-shaped microfluidic system and a method for checking a blood condition having advantages of extracting plasma by centrifuging blood and simultaneously checking a blood condition.

Technical Solution

An exemplary embodiment of the present invention provides a method for checking a blood condition, including: supplying blood to a centrifugal container of a disk; centrifuging the blood in the centrifugal container to isolate blood cells and plasma by rotating the disk and detecting an actual moving distance of the blood cells in the centrifugal container every hour; and calculating a first curve representing the actual moving distance of the blood cells in the centrifugal container every hour and a second curve representing a theoretical moving distance of the blood cells every hour, and calculating hematocrit of the blood and viscosity of the plasma by comparing the first curve and the second curve.

The detecting of the actual moving distance of the blood cells may use an image acquired by photographing the inside of the centrifugal container every hour.

The detecting of the actual moving distance of the blood cells may be performed by calculating a center of mass with respect to a dark area by analyzing a contrast in the image and measuring a short distance of the dark area based on the center of mass.

The calculating of the hematocrit of the blood may be performed by calculating the second curve by using the following equation, and calculating the following $\theta$ after applying the following $r_p$ as the actual moving distance of the blood cells every hour.

$$\frac{\pi}{6}p_p d_p^3 r''_p = \frac{\pi}{6}(p_p - p_f)d_p^3 w^2 r_p - 3\pi d_p r'_p \left\{ u_f(1 + \theta^{1/3}) \exp\left[\frac{5\theta}{3(1-\theta)}\right] \right\}$$

In the equation, $\pi$ is a circle constant, $p_p$ is the density of the blood, $d_p$ is a diameter of the blood cell, $r''_p$ is a moving acceleration of the blood cell, $p_f$ is the density of the plasma, $w$ is an angular velocity of the disk, $r_p$ is a moving distance of the blood cell, $r'_p$ is a moving speed of the blood cell, $u_f$ is the viscosity of the plasma, and $\theta$ is a volume ratio of the blood cells to the entire volume of the blood.

The calculating of the viscosity of the plasma may be performed by calculating the second curve by using the following equation and calculating the following functions $u_f$ after applying the following $r_p$ as the actual moving distance of the blood cells every hour.

$$\frac{\pi}{6}p_p d_p^3 r''_p = \frac{\pi}{6}(p_p - p_f)d_p^3 w^2 r_p - 3\pi d_p r'_p \left\{ u_f(1 + \theta^{1/3}) \exp\left[\frac{5\theta}{3(1-\theta)}\right] \right\}$$

In the equation, $\pi$ is a circle constant, $p_p$ is the density of the blood, $d_p$ is a diameter of the blood cell, $r''_p$ is a moving acceleration of the blood cell, $p_f$ is the density of the plasma, $w$ is an angular velocity of the disk, $r_p$ is a moving distance of the blood cell, $r'_p$ is a moving speed of the blood cell, $u_f$ is the viscosity of the plasma, and $\theta$ is a volume ratio of the blood cells to the entire volume of the blood.

Another exemplary embodiment of the present invention provides a disk-shaped microfluidic system, including: a disk including a centrifugal container to which blood is supplied and centrifuging the blood in the centrifugal container to isolate blood cells and plasma; a photographing unit positioned at the upper side of the disk and photographing an inside of the centrifugal container every hour; and a controller connected with the photographing unit, detecting an actual moving distance of the blood cells in the centrifugal container every hour by using the image photographed by the photographing unit, calculating a first curve representing the actual moving distance of the blood cells in the centrifugal container every hour and a second curve representing a theoretical moving distance of the blood cells every hour, and calculating hematocrit of the blood and viscosity of the plasma by comparing the first curve and the second curve.

The controller may calculate the second curve by using the following equation, and may calculate the following $\theta$ after applying the following $r_p$ as the actual moving distance of the blood cells every hour to calculate hematocrit of the blood.

$$\frac{\pi}{6}p_p d_p^3 r''_p = \frac{\pi}{6}(p_p - p_f)d_p^3 w^2 r_p - 3\pi d_p r'_p \left\{ u_f(1 + \theta^{1/3}) \exp\left[\frac{5\theta}{3(1-\theta)}\right] \right\}$$

In the equation, $\pi$ is a circle constant, $p_p$ is the density of the blood, $d_p$ is a diameter of the blood cell, $r''_p$ is a moving acceleration of the blood cell, $p_f$ is the density of the plasma, $w$ is an angular velocity of the disk, $r_p$ is a moving distance of the blood cell, $r'_p$ is a moving speed of the blood cell, $u_f$ is the viscosity of the plasma, and $\theta$ is a volume ratio of the blood cells to the entire volume of the blood.

The controller may calculate the second curve by using the following equation, and may calculate the following $u_f$ after applying the following $r_p$ as the actual moving distance of the blood cells every hour to calculate viscosity of the plasma.

$$\frac{\pi}{6} p_p d_p^3 r_p'' = \frac{\pi}{6}(p_p - p_f)d_p^3 w^2 r_p - 3\pi d_p r_p' \left\{ u_f (1+\theta^{1/3})\exp\left[\frac{5\theta}{3(1-\theta)}\right]\right\}$$

In the equation, $\pi$ is a circle constant, $p_p$ is the density of the blood, $d_p$ is a diameter of the blood cell, $r''_p$ is a moving acceleration of the blood cell, $p_f$ is the density of the plasma, $w$ is an angular velocity of the disk, $r_p$ is a moving distance of the blood cell, $r'_p$ is a moving speed of the blood cell, $u_f$ is the viscosity of the plasma, and $\theta$ is a volume ratio of the blood cells to the entire volume of the blood.

The disk may further include: a plasma container connected with a centrifugal container; and a micro-valve connected between the centrifugal container and the plasma container.

Advantageous Effects

According to the exemplary embodiment of the present invention, it is possible to provide a disk-shaped microfluidic system and a method for checking a blood condition that extracts plasma by centrifuging blood and simultaneously checks a blood condition.

MODE FOR INVENTION

Figure 1:
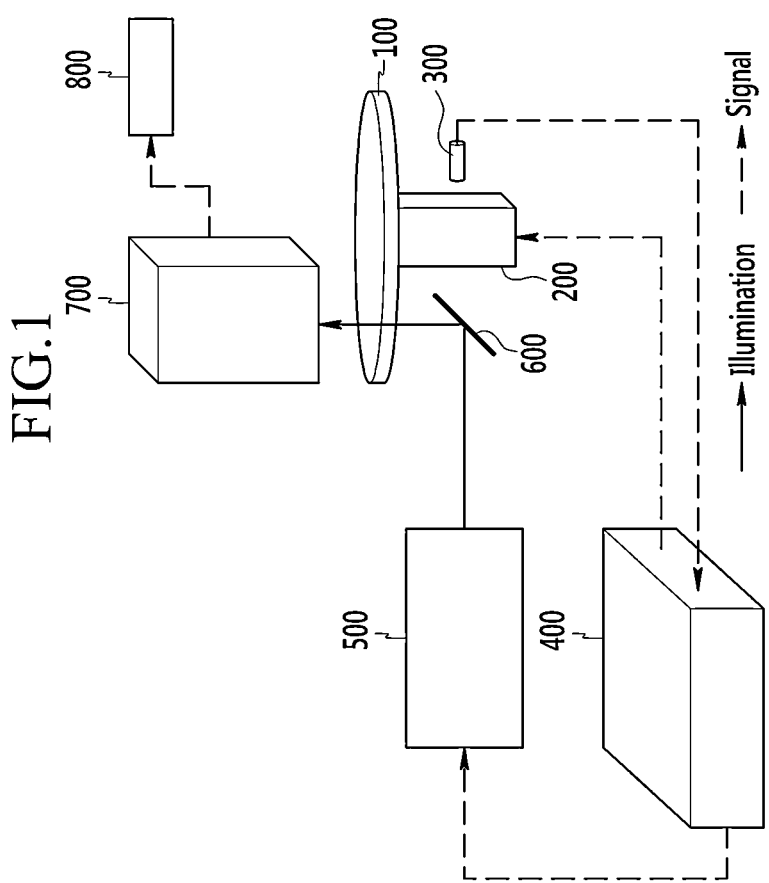
FIG. 1 is a diagram illustrating a disk-shaped microfluidic system according to a first exemplary embodiment of the present invention.

The present invention will be described more fully hereinafter with reference to the accompanying drawings, in which exemplary embodiments of the invention are shown. As those skilled in the art would realize, the described embodiments may be modified in various different ways, all without departing from the spirit or scope of the present invention.

The drawings and description are to be regarded as illustrative in nature and not restrictive. Like reference numerals designate like elements throughout the specification.

Further, the size and thickness of each configuration shown in the drawings are arbitrarily shown for understanding and ease of description, but the present invention is not limited thereto.

In the drawings, for better understanding and ease of description, the thickness of some layers and areas is exaggerated. It will be understood that when an element such as a layer, film, region, or substrate is referred to as being "on" another element, it can be directly on the other element or intervening elements may also be present.

In addition, unless explicitly described to the contrary, the word "comprise" and variations such as "comprises" or "comprising" will be understood to imply the inclusion of stated elements but not the exclusion of any other elements. Further, in the specification, the word "on" means positioning on or below the object portion, but does not essentially mean positioning on the lower side of the object portion based on a gravity direction.

Hereinafter, a disk-shaped microfluidic system according to a first exemplary embodiment of the present invention will be described with reference to FIGS. 1 to 2.

FIG. 1 is a diagram illustrating a disk-shaped microfluidic system according to a first exemplary embodiment of the present invention.

As illustrated in FIG. 1, the disk-shaped microfluidic system according to the first exemplary embodiment of the present invention centrifuges blood and simultaneously checks a blood condition, and includes a disk 100, a driver 200, a sensor 300, an adjustor 400, an illuminator 500, a mirror 600, a photographing unit 700, and a controller 800.

Figure 2:
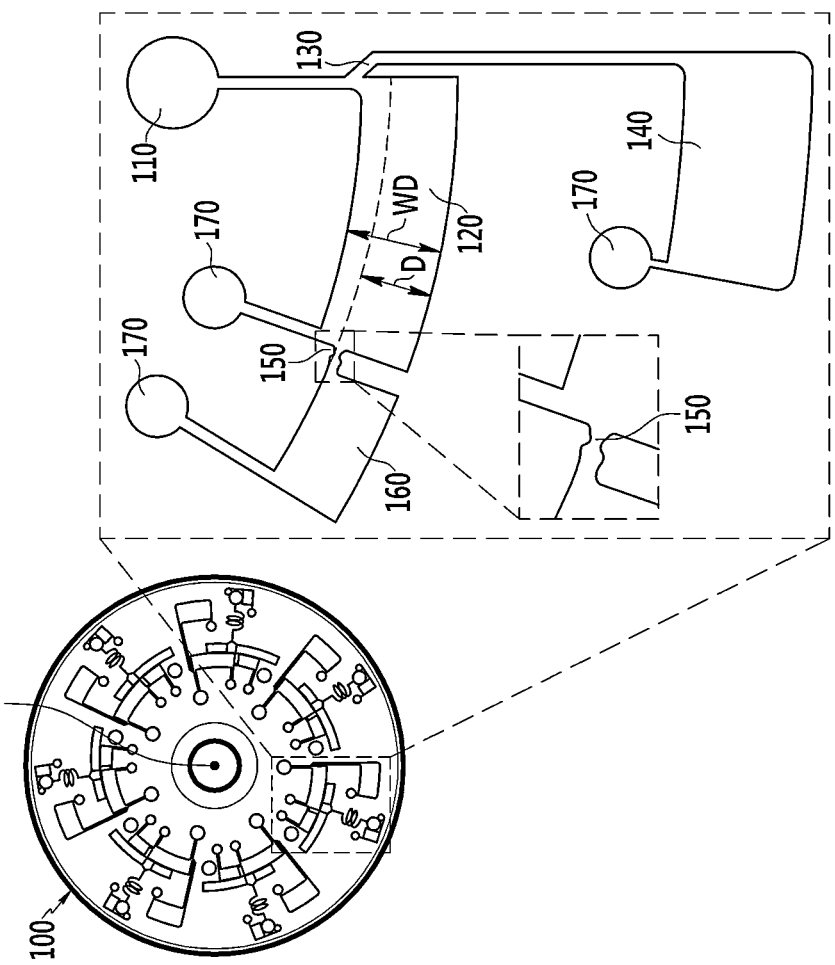
FIG. 2 is a diagram illustrating a disk illustrated in FIG. 1.

FIG. 2 is a diagram illustrating a disk illustrated in FIG. 1.

As illustrated in FIG. 2, the disk 100 has a circular disk shape, and centrifuges blood supplied from the outside to blood cells and plasma by rotating itself based on a central axis C. In the disk 100, an injection port 110, a centrifugal container 120, a waste flow channel 130, a waste receiving container 140, a micro-valve 150, a plasma container 160, and an air discharge port 170 may be formed by intaglio through a mass production method, such as injection molding using MEMS technology such as photolithography or a molding insert having an opposite shape, hot embossing, UV-molding, and casting. The disk 100 may be made of a metal material, a ceramic material, and a polymer material, such as cyclic olefin copolymer (COC), polymethylmethacrylate (PMMA), polystyrene (PS), polycarbonate (PC), polydimethylsiloxane (PDMS), polytetrafluoroethylene (Teflon), and polyvinylchloride (PVC).

The injection port 110 is adjacent to the central shaft C to be disposed in the disk 100, and is a passage to which blood is supplied.

The centrifugal container 120 is connected with the injection port 110, and is a container in which the blood supplied from the injection port 110 is placed. When the disk 100 rotates, the blood is centrifuged to blood cells and plasma in the centrifugal container 120.

The waste flow channel 130 is a passage which is positioned between the centrifugal container 120 and the injection port 110, and through which the blood overflowing from the centrifugal container 120 moves to the waste receiving container 140 while rotating the disk 100.

The waste receiving container 140 is a container which is connected with the centrifugal container 120 by the waste flow channel 130, and receives the blood flowing from the centrifugal container 120 while rotating the disk 100.

The micro-valve 150 is a passage which is connected between the centrifugal container 120 and the plasma container 160, of which a position is determined by considering hematocrit of the blood, and through which only the centrifuged plasma passes in the centrifugal container 120 by determining the position thereof. In more detail, the micro-valve 150 may be disposed to correspond to one width D of 30% to 60% of an entire width WD of the centrifugal container 120 by considering 30% to 60% which is a general range of the hematocrit. The micro-valve 150 may adjust opening and closing according to an angular velocity of the disk 100. In detail, the opening and closing of the micro-valve 150 is adjusted due to a difference between a first pressure formed around the micro-valve 150 by centrifugal force according to rotation of the disk 100 and a second pressure formed by surface tension in the micro-valve 150. For example, when the first pressure is larger than the second pressure, the micro-valve 150 opens and the plasma moves to the plasma container 160 from the centrifugal container 120 through the micro-valve 150, and when the second pressure is larger than the first pressure, the micro-valve 150 closes and the blood does not move to the plasma container 160 from the centrifugal container 120 through the micro-valve 150. Since the first pressure is proportional to the angular velocity of the disk 100, the second pressure is adjusted to be larger than the first pressure when the blood is centrifuged, and the first pressure is adjusted to be larger than the second pressure when the plasma is extracted by adjusting the angular velocity of the disk 100, and as a result, each of the closing and the opening of the micro-valve 150 may be adjusted in response to each of the centrifugation and the plasma extraction by adjusting the angular velocity of the disk 100.

The plasma container 160 is a container which is connected with the centrifugal container 120 through the micro-valve 150 to receive the plasma centrifuged from the blood in the centrifugal container 120. The plasma received in the plasma container 160 may move to another container through one channel connected with the plasma container 160 to be stored.

The air discharge port 170 is connected to each of the centrifugal container 120, the waste receiving container 140, and the plasma container 160, and a passage through which air in each container is discharged, when a fluid such as blood and plasma are supplied to each container.

Hereinafter, extracting the plasma in the disk of the disk-shaped microfluidic system according to the first exemplary embodiment of the present invention will be described with reference to FIG. 3.

Figure 3:
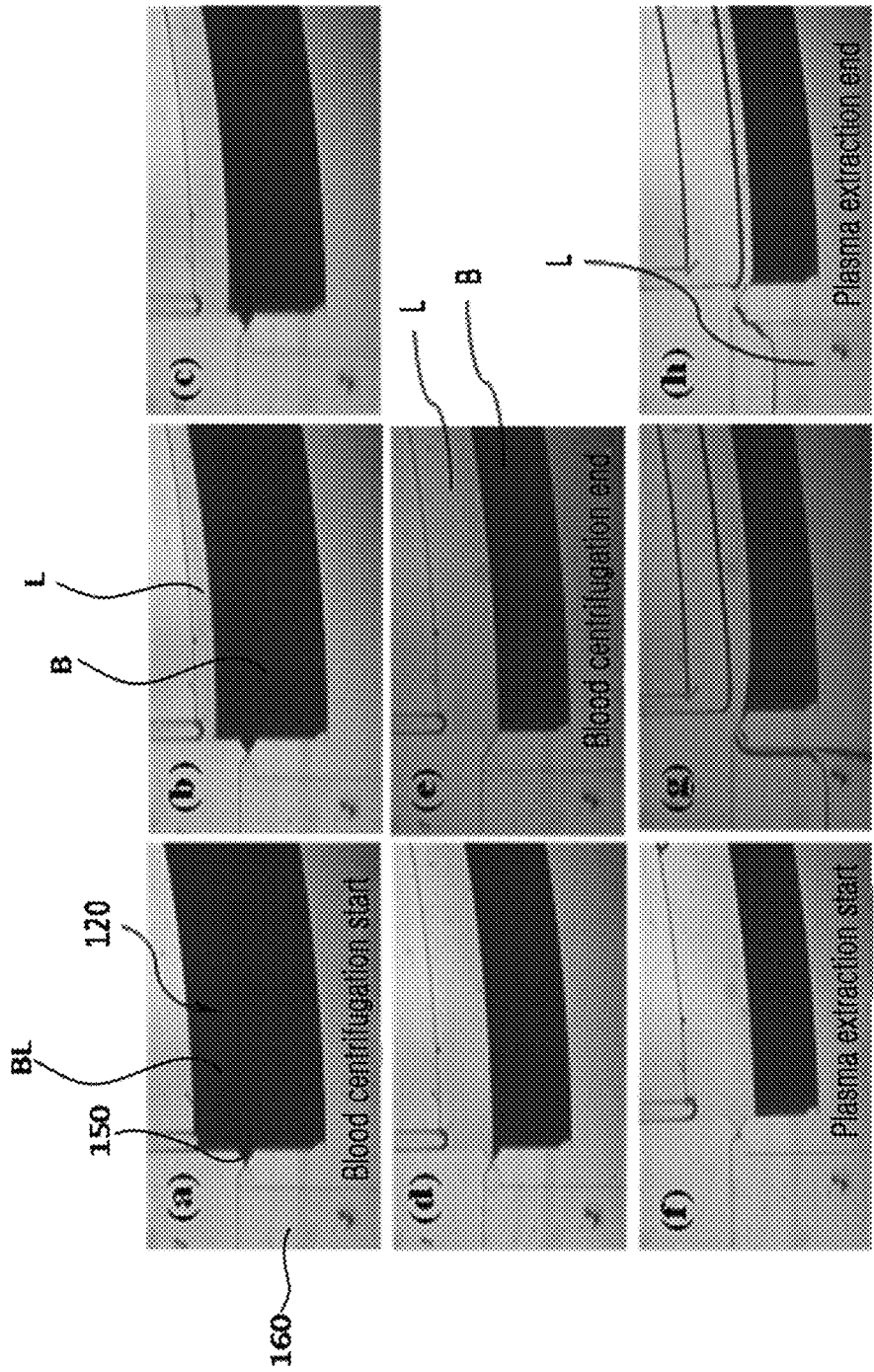
FIGS. 3(a) to 3(h) are photographs illustrating plasma extracted by using the disk-shaped microfluidic system according to the first exemplary embodiment of the present invention.

FIG. 3 is a photograph illustrating plasma extracted from the disk of the disk-shaped microfluidic system according to the first exemplary embodiment of the present invention.

FIG. 3 (a) to (h) are photographs illustrating a test process of centrifugation of a small amount of blood and plasma extraction performed by using the disk 100 of an actually manufactured disk-shaped microfluidic system as time passes. As illustrated in FIG. (a) to (e), centrifugation of blood BL injected into the centrifugal container 120 by centrifugal force which is caused by rotating the disk 100 is performed. In this process, as illustrated in FIG. 3 (b), the blood BL is accurately divided into blood cells B and plasma L, and the blood cells B are precipitated in an outer direction of a rotation center, and are not precipitated any more after a predetermined time as illustrated in FIG. 3 (e). Further, while the centrifugation of the blood BL is performed, the movement of the blood or the plasma is prevented by the micro-valve 150.

Thereafter, the micro-valve 150 is opened by increasing the angular velocity of the disk 100 to induce the extraction of the centrifuged plasma L. As illustrated in FIG. 3 (f) to (h), the plasma L separated on an upper portion of the centrifugal container 120 moves to the plasma container 160 through the micro-valve 150. As a result, it may be verified that a small amount of blood may be centrifuged and the plasma may be extracted by a convenient and efficient method using the disk 100 of the disk-shaped microfluidic system according to the first exemplary embodiment of the present invention.

Referring back to FIG. 1, the driver 200 supports the disk 100, and includes a driving means of a motor and the like to rotate the disk 100.

The sensor 300 is positioned to be adjacent to the disk 100 and serves to sense the number of revolutions of the disk 100.

The adjustor 400 is connected with the sensor 300 and the driver 200, and serves to receive a signal from the sensor 300 sensing the number of revolutions of the disk 100 to adjust the rotation of the disk 100 by the driver. The angular velocity of the disk 100 may be adjusted by the adjustor 400.

The illuminator 500 is connected with the adjustor 400, and reflects an illumination to the mirror 600 in a flash shape in synchronization with the number of revolutions of the disk 100.

The mirror 600 is positioned at a lower side of the disk 100, and reflects the illumination irradiated from the illuminator 500 in a disk 100 direction.

The photographing unit 700 is positioned at the upper side of the disk 100 to correspond to the centrifugal container 120 of the disk 100 and the mirror 600, and photographs an inside of the centrifugal container 120 every hour by using the illumination in synchronization with the number of revolutions of the disk. The photographing unit 700 photographs the inside of the centrifugal container 120 every hour.

The controller 800 is connected with the photographing unit 700, detects an actual moving distance of the blood cells in the centrifugal container 120 every hour by using the image photographed by the photographing unit 700, calculates a first curve showing an actual moving distance of the blood cells every hour and a second curve showing a theoretical moving distance of the blood cells every hour, and calculates hematocrit of the blood and viscosity of the plasma by comparing the first curve and the second curve. That is, the controller 800 calculates the hematocrit of the blood and viscosity of the plasma which are centrifuged in the disk 100 to check the blood condition.

The controller 800 calculates the second curve by using the following equation, and calculates the following θ after applying the following $r_p$ as the actual moving distance of the blood cells every hour to calculate the hematocrit of the blood.

$$\frac{\pi}{6} p_p d_p^3 r_p'' = \frac{\pi}{6}(p_p - p_f)d_p^3 w^2 r_p - 3\pi d_p r_p' \left\{ u_f(1+\theta^{1/3})\exp\left[\frac{5\theta}{3(1-\theta)}\right]\right\}$$ [Equation]

In the equation, π is a circle constant, $p_p$ is the density of the blood, $d_p$ is a diameter of the blood cell, $r''_p$ is a moving acceleration of the blood cell, $p_f$ is the density of the plasma, w is an angular velocity of the disk, $r_p$ is a moving distance of the blood cell, $r'_p$ is a moving speed of the blood cell, $u_f$ is the viscosity of the plasma, and θ is a volume ratio of the blood cells to the entire volume of the blood.

Further, the controller 800 calculates the second curve by using the equation, and calculates the $u_f$ after applying the $r_p$ as the actual moving distance of the blood cell every hour to calculate the viscosity of the plasma.

Hereinafter, a method for checking a blood condition according to a second exemplary embodiment of the present invention using the disk-shaped microfluidic system according to the first exemplary embodiment of the present invention described above will be described with reference to FIGS. 4 and 5.

Figure 4:
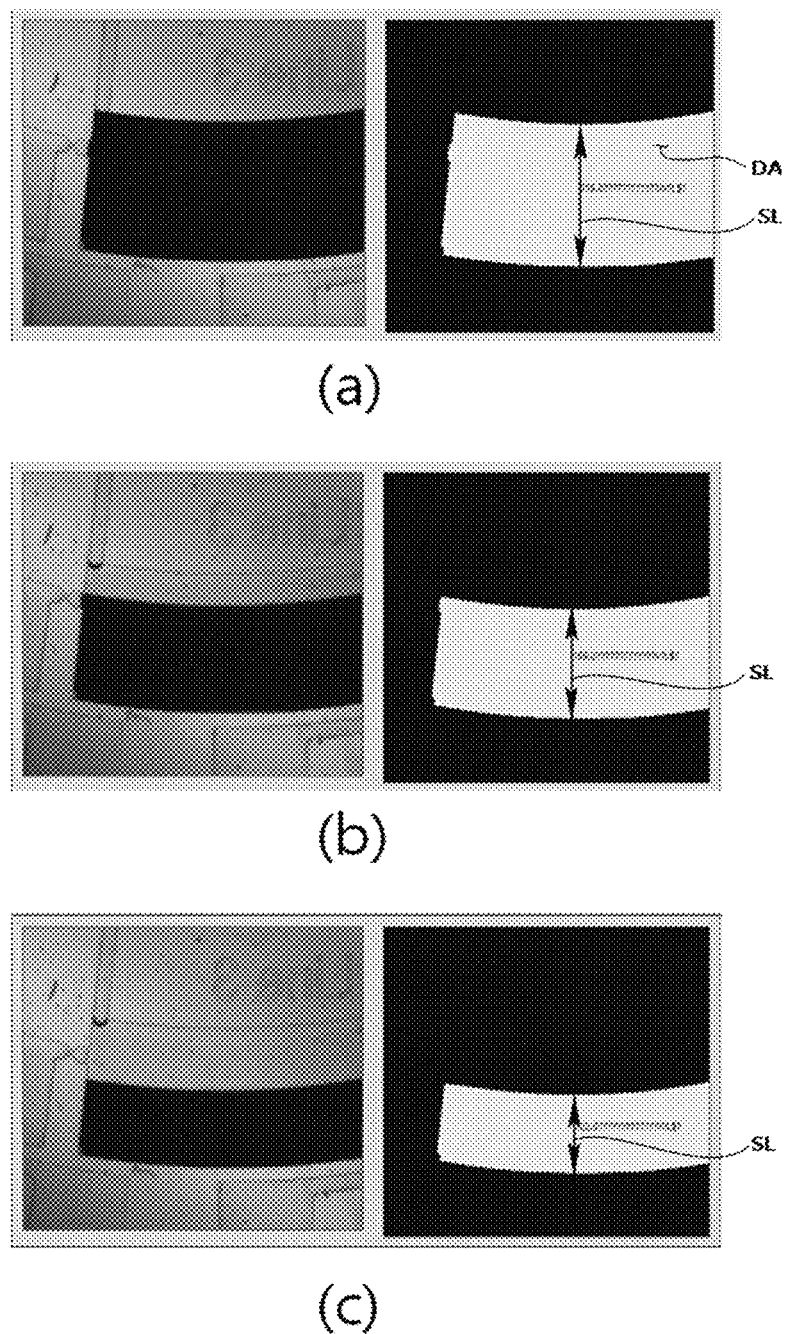
FIGS. 4(a) to 4(c) and 5 are diagrams for describing a method for checking a blood condition according to a second exemplary embodiment of the present invention.
Figure 5:
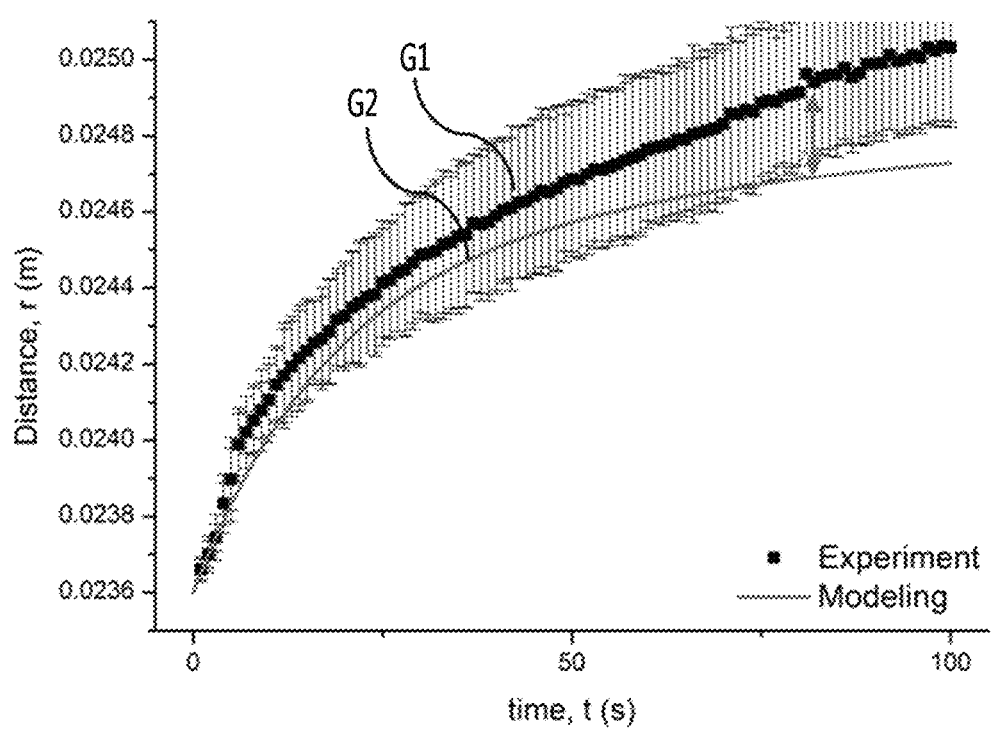

FIGS. 4 and 5 are diagrams for describing a method for checking a blood condition according to a second exemplary embodiment of the present invention.

First, the blood is supplied to the centrifugal container 120 of the disk 100.

Next, the blood in the centrifugal container 120 is centrifuged into blood cells and plasma by rotating the disk 100, and an actual moving distance of the blood cells in the centrifugal container 120 every hour is detected.

FIG. 4 is a photograph illustrating an image photographed the inside of the centrifugal container every hour.

In detail, as illustrated in FIG. 4, original images (left image of each of FIGS. 4 (a), (b), and (c)) photographing the inside of the centrifugal container 120 every hour are corrected to post-images (right image of each of FIGS. 4 (a), (b), and (c)) by analyzing a contrast. In this case, in the post-image, the precipitation of the blood cells is changed to white, and the background is changed to black. Thereafter, a center of mass for a dark area (DA) which is the precipitation of the blood cells of the post-image is calculated, and a short distance (SL) of the dark area (DA) is measured based on the center of mass to detect the actual moving distance of the blood cells in the centrifugal container 120 every hour. Such a process is performed with respect to the entire image frame, and as a result, data showing a precipitated height of the blood cells with time may be obtained. The detection may be performed by the controller 800.

Next, the hematocrit of the blood and the viscosity of the blood cells are calculated.

In detail, the first curve showing the actual moving distance of the blood cells every hour and the second curve showing the theoretical moving distance of the blood cells every hour are calculated, and the hematocrit of the blood and the viscosity of the blood cells are calculated by comparing the first curve and the second curve.

Hereinafter, a method of calculating each of the hematocrit of the blood and the viscosity of the blood cells will be described in more detail.

FIG. 5 is a graph illustrating a first curve showing the actual moving distance of the blood cells every hour and a second curve showing the theoretical moving distance of the blood cells every hour. An X axis of FIG. 5 is a time (second) axis, and a Y axis is a moving distance (m) axis of the blood cells.

As illustrated in FIG. 5, a first curve G1 which is an experimental curve showing the actual moving distance of the blood cells every hour is detected by analyzing the image obtained through the photographing unit 700 of the disk-shaped microfluidic system, as described above.

A second curve G2 which is a theoretical curve showing the theoretical moving distance of the blood cells every hour is calculated by the following equation.

$$\frac{\pi}{6} p_p d_p^3 r''_p = \frac{\pi}{6}(p_p - p_f)d_p^3 w^2 r_p - 3\pi d_p r'_p \left\{ u_f (1+\theta^{1/3}) \exp\left[\frac{5\theta}{3(1-\theta)}\right] \right\}$$ [Equation]

In the equation, $\pi$ is a circle constant, $p_p$ is the density of the blood, $d_p$ is a diameter of the blood cell, $r''_p$ is a moving acceleration of the blood cell, $p_f$ is the density of the plasma, w is an angular velocity of the disk, $r_p$ is a moving distance of the blood cell, $r'_p$ is a moving speed of the blood cell, $u_f$ is the viscosity of the plasma, and $\theta$ is a volume ratio of the blood cells to the entire volume of the blood.

The equation is configured based on a dynamic force balance formed by a plurality of globular particles, when the globular particles existing in a specific fluid are precipitated by centrifugal force. First, when one globular particle is precipitated by centrifugal force in the specific fluid, movement of the particle forms a dynamic force balance by centrifugal force, buoyancy force, and drag force, and after the blood cell is assumed as a rigid body, that is, a particle without deformation, a viscosity value of the fluid including a plurality of particles instead of the viscosity of the fluid is applied by considering a condition where the plurality of particles are precipitated, and as a result, the equation is deducted by mathematizing the condition.

Iteration is performed based on the equation to calculate the second curve G2. When the second curve G2 is calculated, $r''_p$, $r'_p$, and $r_p$ are calculated by applying predetermined theoretical values to $\pi$, $p_p$, $d_p$, $p_f$, w, $u_f$, and $\theta$.

The hematocrit of the blood and the viscosity of the plasma are calculated by comparing the first curve G1 and the second curve G2.

First, in the hematocrit of the blood, when a curve which is most similar to the first curve G1 is found by changing $\theta$ which is the volume ratio of the blood cells to the entire volume of the blood when the second curve G2 is calculated, a percentage of $\theta$ which is the volume ratio at this time becomes an actual hematocrit value of the blood which is centrifuged in the centrifugal container 120 of the disk 100. For example, when $r_p$ is applied as the actual moving distance of the blood cell every hour of the first curve G1, $\theta$ is calculated by using the equation to calculate the hematocrit value of the blood.

Next, the viscosity of the plasma is smaller than the theoretical value when the moving speed of the blood cell shown in the first curve G1 is faster than $r'_p$ which is the moving speed of the blood cell of the second curve G2, and is larger than the theoretical value when the moving speed of the blood cell showed in the first curve G1 is slower than $r'_p$ which is the moving speed of the blood cell of the second curve G2. The actual viscosity value of the plasma is predicted by such an inference method. For example, it is considered that a period of 0 to 50 seconds of the curve is a period which is influenced most by the viscosity of the plasma in the centrifugation of the blood, and the viscosity of the plasma may be determined. In comparison with the theoretical curve, when the moving speed of the particles shown in the experimental curve is fast, the viscosity of the plasma is smaller than the theoretical value, and when the moving speed of the particles shown in the experimental curve is slow, the viscosity of the plasma is larger than the theoretical value. The actual viscosity value of the plasma is predicted by such an inference method. When $r_p$ is applied as the actual moving distance of the blood cells every hour shown in the first curve G1, $u_f$ is calculated by using the equation to calculate the viscosity of the plasma.

As such, by comparing the first curve G1 which is the experimental curve showing development of the blood centrifugation and the second curve G2 which is the theoretical curve, the hematocrit of the blood and the viscosity of the plasma which are important properties of the blood may be calculated, and the calculated hematocrit of the blood and viscosity of the plasma may be used as a criterion for estimating the blood condition.

As described above, by the disk-shaped microfluidic system according to the first exemplary embodiment of the present invention and the method for checking the blood condition according to the second exemplary embodiment of the present invention, the blood is centrifuged to extract the plasma, and simultaneously the blood condition is checked, and as a result, additional equipment for checking the blood condition is not required, and additional time for checking the blood condition is not required.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. A method for checking a blood condition, the method comprising:
supplying blood to a centrifugal container of a disk;
centrifuging the blood in the centrifugal container to separate plasma from blood cells by rotating the disk;
detecting an actual moving distance of the blood cells in the centrifugal container every hour;
calculating a first curve representing the actual moving distance of the blood cells in the centrifugal container every hour;
calculating a second curve representing a theoretical moving distance of the blood cells every hour; and
calculating hematocrit of the blood and viscosity of the plasma by comparing the first curve and the second curve,
wherein:
the calculating of the second curve is performed by using the following equation, $$\frac{\pi}{6} p_p d_p^3 r_p'' = \frac{\pi}{6}(p_p - p_f) d_p^3 w^2 r_p - 3\pi d_p r_p' \left\{ u_f(1+\theta^{1/3}) \exp\left[\frac{5\theta}{3(1-\theta)}\right] \right\},$$

in the equation, $r''_p$, $r'_p$, and $r_p$ are calculated by applying predetermined theoretical values to $\pi$, $p_p$, $d_p$, $p_f$, w, $u_f$, and $\theta$, $\pi$ is a circle constant, $p_p$ is a density of the blood, $d_p$ is a diameter of a blood cell, $r''_p$ is a moving acceleration of the blood cell, $p_f$ is a density of the plasma, w is an angular velocity of the disk, $r_p$ is a moving distance of the blood cell, $r'_p$ is a moving speed of the blood cell, $u_f$ is the viscosity of the plasma, and $\theta$ is a volume ratio of the blood cells to an entire volume of the blood,
the calculating of the hematocrit of the blood is performed by calculating $\theta$ in the equation after applying $r_p$ as the actual moving distance of the blood cells every hour of the first curve, and
the calculating of the viscosity of the plasma is performed by calculating $u_f$ in the equation after applying $r_p$ as the actual moving distance of the blood cells ever hour of the first curve.

2. The method of claim 1, wherein
the detecting of the actual moving distance of the blood cells uses an image acquired by photographing the inside of the centrifugal container every hour.

3. The method of claim 2, wherein
the detecting of the actual moving distance of the blood cells is performed by calculating a center of mass with respect to a dark area by analyzing a contrast in the image and measuring a short distance of the dark area based on the center of mass.

* * * * *